United States Patent
Oglevee-O'Donovan et al.

(10) Patent No.: US 6,610,909 B1
(45) Date of Patent: Aug. 26, 2003

(54) METHOD FOR THE COMMERCIAL PRODUCTION OF TRANSGENIC PLANTS

(75) Inventors: Wendy Oglevee-O'Donovan, Scottsdale; Richard N. Arteca; Jeannette Arteca, both of State College; Eleanor Stoots, Connellsville, all of PA (US)

(73) Assignee: Penn State Research Foundation, University Park, PA (US)

( * ) Notice: Subject to any disclaimer, the term of this patent is extended or adjusted under 35 U.S.C. 154(b) by 0 days.

(21) Appl. No.: 08/555,755

(22) Filed: Nov. 9, 1995

Related U.S. Application Data

(63) Continuation-in-part of application No. 08/149,702, filed on Nov. 9, 1993, now Pat. No. 5,514,580, which is a continuation of application No. 07/690,073, filed on Apr. 23, 1991, now abandoned.

(51) Int. Cl.[7] ............................. A01H 5/00; C12N 15/82
(52) U.S. Cl. ....................... 800/311; 800/283; 800/286; 800/294
(58) Field of Search ........................ 800/205, DIG. 22, 800/283, 286, 294, 311; 435/172.3, 320.1, 410, 419, 252.3

(56) References Cited

U.S. PATENT DOCUMENTS

| | | | |
|---|---|---|---|
| 5,276,268 A | 1/1994 | Strauch et al. | 800/205 |
| 5,283,184 A | 2/1994 | Jorgensen et al. | 435/172.3 |
| 5,286,635 A | 2/1994 | Hanson et al. | 4335/172.3 |

OTHER PUBLICATIONS

Messens et al., Proc. Natl. Acad. Sci. USA. vol. 87, pp. 4368–4372, Jun. 1990.*
Marsolais et al., "Somatic embryogenesis and artificial seed production in Zonal . . . ", Can J. Bot. 69: 1188–1993 (1991).
Skirvin et al., "Tissue Culture–induced Variation in Scented Pelargonium spp", J. Amer. Soc. Hort. Sci. 101(3) 281–290 (1976).
Cassells et al. "Adventitious Regeneration In Pelargonium X Domesticum Baily", Acta Horticulturae 212, 419–425 (1987).
Pellegrineschi et al., "Improvement of Ornamental Characters and Fragrance Production . . . ", Bio/Technology, vol. 12, 64–68 (1994).
van der Krol et al., "Antisense chalcone synthase genes in petunia: Visualization of . . . ", Mol Gen Genet 220, 204–212 (1990).

\* cited by examiner

*Primary Examiner*—Amy J. Nelson
(74) *Attorney, Agent, or Firm*—Webb Ziesenheim Bruening Logsdon Orkin & Hanson, P.C.

(57) ABSTRACT

A process for commercially propagating plants by tissue culture in such a way as both to conserve desired plant morphology and to transform the plant with respect to one or more desired genes. The method includes the steps of (a) creating an Agrobacterium vector containing the gene sequence desired to be transferred to the propagated plant, preferably together with a marker gene; (b) taking one or more petiole explants from a mother plant and inoculating them with the Agrobacterium vector; (c) conducting callus formation in the petiole sections in culture, in the dark; and (d) culturing the resulting callus in growth medium containing a benzylamino growth regulator such as benzylaminopurine or, most preferably, benzylaminopurineriboside. Additional optional growth regulators including auxins and cytokinins (indole butyric acid, benzylamine, benzyladenine, benzylaminopurine, alpha naphthylacetic acid and others known in the art) may also be present. Preferably, the petiole tissue is taken from *Pelargonium x domesticum* and the Agrobacterium vector contains an antisense gene for ACC synthase or ACC oxidase to prevent ACC synthase or ACC oxidase expression and, in turn, the ethylene formation for which these enzymes are precursors.

17 Claims, No Drawings

METHOD FOR THE COMMERCIAL PRODUCTION OF TRANSGENIC PLANTS

CROSS-REFERENCE TO RELATED APPLICATIONS

This application is a Continuation-in-part application based upon U.S. application Ser. No. 08/149,702 filed Nov. 9, 1993 now U.S. Pat. No. 5,514,580, which is a Continuation of U.S. application Ser. No. 07/690,073 filed Apr. 23, 1991 now abandoned, by Wendy Oglevee-O'Donovan and Eleanor Stoots.

STATEMENT REGARDING FEDERALLY FUNDED RESEARCH

This invention was made with support from the Government under Experiment Station (Hatch Act) Project Nos. 2809 and 3179 awarded by the United States Department of Agriculture. The Government had certain rights in the invention.

Field of the Invention

This invention relates to the development of techniques for the commercial production of transgenic plants.

Background of the Invention

The genetic manipulation of plants is centuries old, and modern crop yields and disease- and pest-resistances often owe much to traditional plant genetic engineering. Classical plant breeding methods are time-consuming and subject to chance, however, so the recent advent of recombinant DNA techniques is promising. This promise is encouraging especially with respect to enabling plant geneticists to identify and to clone specific genes for desirable traits, and to introduce such genes into already useful varieties of plants.

Translating genetic engineering theory into practice, however, and then furthermore into a commercially practical reality, requires ingenuity. Gene transplantation in plants has already been accomplished at this writing—and examples are cited below—but heretofore no practical method for the commercial production of transgenic plants has been perfected.

Apart from the transgenic plant technology per se, it is known to propagate plants by replicating plant cells in culture, or "tissue culture." An early motivating force in the development of tissue culture was the desire to improve upon the relatively slow and low yields of vegetative propagation with the quick and exponential proliferation of new plants from cell culture. Tissue culture methods are made possible by the plant physiological phenomenon of callus formation. When a plant is wounded, a patch of soft cells called a calli grows over the wound and, with time, phenolic compounds accumulate in the soft cells and harden, effectively sealing the wound. While hardened callus is the plant equivalent of scar tissue, callus is different from mammalian scar tissue with respect to its regenerative properties. If a piece of young, still-soft callus is removed and placed in a culture medium containing salts, sugars, vitamins, amino acids and the appropriate plant growth hormones, rather than harden, the cells will continue to divide and give rise to a disorganized mass of undifferentiated cells called a "callus culture." Plant or seedling "explants," or tissue samples, will likewise grow into similar cell cultures. The cultured cells can further be induced to redifferentiate into shoots, roots or whole plants by further culturing with the necessary hormones and growth media.

One of the most serious drawbacks with tissue culture propagation techniques has been the morphologic variation from generation to generation, a problem which is particularly notable in certain species and varieties. For example, as reported in Cassells, A. C., and Carney, B. F., "Adventitious regeneration in *Pelargonium x domesticum* Bailey," *Acta Horticulturae,* 212(II), 419–425 (1987), in stem and petiole tissue cultures of Grand Slam (as an example of *P. domesticum,* also known as Regal Pelargoniums or "Martha Washington" geraniums), up to 16% of the adventitious regenerants were variants, depending on the explant origin. The authors concluded that genome instability in Grand Slam and presumably other *P. domesticum* varieties may produce useful variation but mitigates against the use of adventitious regeneration in micropropagation.

The findings of Cassells et al. are consistent with the earlier work of Skirvin, R. M. and Janick, Jules, "Tissue Culture-Induced Variation in Scented Pelargonium ssp.," *J. Amer. Soc. Hort. Sci.,* 101(3), 281–290 (1976). Skirvin et al. compared tissue culture propagated Pelargonium plants (from root cuttings, petiole cuttings or calliclones) with plants derived from vegetative propagation, i.e., stem cuttings. The plants derived from stem cuttings were all uniform and identical to the parental clone, whereas those from the root cuttings, petiole cuttings or calliclones were all morphologically distinct with the degree of variability depending upon the cultivar. The authors conclude that the variability associated with calliclones derived from tissue culture is a pool on which selection can be imposed, implying conversely that tissue culturing of this type is inappropriate for use in attempting reliable regeneration of *Pelargonium x domesticum* varieties.

Other varieties and species, besides *Pelargonium x domesticum,* are known and/or believed to suffer morphologic variation when propagated using tissue culture. It can be easily appreciated that any substantial morphologic variation in propagation is unacceptable for commercial propagation of a desired variety or species. Thus, tissue culture methods are not always acceptable for commercial use, even with the potentially much larger yields achievable as compared with prior art vegetative propagation techniques.

Apart from tissue culture considerations, gene transplantation in plants has achieved some success at this writing. Gene introduction is generally accomplished with a vector such as Agrobacterium. As this technology developed, it was noted that Crown Gall tumors of plants arose at the site of infection of some species of the bacterium Agrobacterium. The cells of Crown Galls acquire the properties of independent, unregulated growth. In culture, such transformed cells grow in the absence of the plant hormones usually necessary for plant cell growth, and the cells retain the transformed phenotype even in the absence of the bacterium. The tumor-inducing agent in Agrobacterium is a plasmid that integrates some of its DNA into the chromosome of the host plant cells. Ti (tumor-inducing) plasmids exist in Agrobacterium cells as independently replicating genetic units.

Ti plasmids are maintained in Agrobacterium because part of the plasmid DNA, the T-DNA, carries the genes coding for the synthesis of amino acids called opines. The infected plant cell is induced to synthesize these amino acids, but the plant cannot use these amino acids. The Ti plasmid is believed to carry genes coding for enzymes that can degrade opines. Thus, Ti plasmids both make and degrade opines, within the plant cell, which the plant cell cannot metabolically use—presumably giving a selective advantage to the Agrobacterium at least with respect to utilization of the opine metabolites. A second set of genes in T-DNA codes for enzymes which lead to production of hormones which, in turn, cause the infected plant cell to divide in an unregulated way.

In summary terms, T-DNA enters a plant cell by what amounts to the equivalent of bacterial conjugation between the Agrobacterium and the plant cell. In other words, an Agrobacterium organism and a plant cell transfer their DNA in a process analogous to mating. Ultimately, T-DNA becomes incorporated into the genomic plant cell DNA in the plant cell nucleus.

All of the above background illustrates how Agrobacterium species can serve well as vectors for genetic transformation of plant cells. Early gene transfer using Ti plasmids, T-DNA and Agrobacterium was accomplished by the cointegration method, in which T-DNA was first cloned into a standard *E. coli* cloning vector, and the plant gene was subsequently cloned into a second cloning site carried by the vector. This intermediate vector was introduced into Agrobacterium organisms containing intact Ti plasmids. Recombination occurred between the homologous regions of the intermediate vector and the wild-type Ti plasmid, and on infection of a plant with the Agrobacterium the recombinant plasmid is transferred to the plant cells.

Despite the early use of the cointegration method described above—and certainly it still works—the standard method for T-DNA transfer as of this writing is called the "binary system." The binary system was devised when investigators realized that the essential functions for transfer are supplied separately by the T-DNA itself and by the Ti plasmid, and that the components can be carried on separate vectors. The binary vector contains the borders of the T-DNA—needed for excision and integration—and the hormone-producing region of the original T-DNA can be removed and replaced with the foreign gene sequence intended for transfer to the plant cell. One side benefit of the use of binary vectors is that, by removing the hormone-producing regions of the T-DNA, uncontrolled growth of the recipient cells is prevented—or in other words the tumor-causing aspect of the T-DNA is nullified. The vir genes of the Ti plasmid can be supplied on a separate plasmid and etc.; the binary vector technique for gene transfer into plants is well established at this writing.

An example of the use of binary vectors to introduce functional genes into plants came about through experiments to use antisense RNA to control plant gene expression. Early work used binary vectors to introduce antisense polygalacturonase genes into tomato plants, to turn off the polygalacturonase expression which in turn digests pectin, in attempts to reduce bruising of tomato fruit during shipment. The results of these trials were disappointing. However, when binary vectors have been used to transfer antisense ethylene precursor genes into tomato plants, the results have been favorable. The antisense gene prevents expression of the ethylene precursor, no ethylene production occurs during storage of the harvested tomatoes, and thus no ripening occurs until the time ripening is desired, when the fruit can be contacted with ethylene from another source.

Exemplary publications and patents which disclose transgenic plants and various techniques therefor are summarized below.

Pellegrineschi, A., et al., "Improvement of Ornamental Characters and Fragrance Production in Lemon-scented Geranium Through Genetic Transformation by *Agrobacterium rhizogenes,*" *Bio/Technology,* Vol. 12 (January, 1994) discloses transformation of root cultures by inoculating stem and leaf fragments with *Agrobacterium rhizogenes*. An important plasmid in this species of Agrobacterium is the root-inducing plasmid which can be used to transfer to the plant genome the genes necessary for improved root growth in culture. The use of sterilized petioles as the source of explant material for plant transformation and culture is disclosed.

U.S. Pat. No. 5,276,268 to Strauch et al., entitled "Phosphinothricin-Resistance Gene, and Its Use," is directed to the transfer of phosphinothricin-resistance gene into plants using Agrobacterium species. A modification of the binary vector method is discussed, and the phosphinothricin-resistance gene nucleic acid sequences are provided.

U.S. Pat. No. 5,283,184 to Jorgenson et al. is entitled "Genetic Engineering of Novel Plant Phenotypes" and discusses transgenote formation and propagation in tissue culture, as well mentioning Pelargoniums and geraniums (and many other plants) by name. The tissue culture propagation of morphologically conserved transgenotes is not discussed.

U.S. Pat. No. 5,286,635 to Hanson et al., entitled "Genetically, Transformed Pea Plants and Methods for Their Production," discloses the transfer of desired gene sequences into pea plants by incubating pea plant explants (preferably not callus) with Agrobacterium vectors containing the desired gene sequence. Mature seed material is used as the explant source. The issue of total morphologic conservation is not addressed.

Thus while certain inroads have been made in the area of tissue culture plant propagation as well as in plant gene transfer, a need remains for a method for the commercially viable production of transgenic plants in which the plants undergo only minimal, and thus commercially acceptable, morphologic variation as a result of tissue culture propagation.

SUMMARY OF THE INVENTION

In order to meet this need, the present method is a process for commercially propagating plants by tissue culture in such a way as both to conserve desired plant morphology and to transform the plant with respect to one or more desired genes. The method includes the steps of (a) creating an Agrobacterium vector containing the gene sequence desired to be transferred to the propagated plant, preferably together with a marker gene; (b) taking one or more petiole explants from a mother plant and inoculating them with the Agrobacterium vector; (c) conducting callus formation in the petiole sections in culture, in the dark; and (d) culturing the resulting callus in growth medium having a benzylamino growth regulator such as benzylaminopurine or, most preferably, benzylaminopurineriboside. Additional optional growth regulators including auxins and cytokinins (indole butyric acid, benzylamine, benzyladenine, benzylaminopurine, alpha naphthylacetic acid and others known in the art) may also be present. Preferably, the petiole tissue is taken from *Pelargonium x domesticum* and the Agrobacterium vector contains an antisense gene for ACC synthase or ACC oxidase to prevent ACC synthase or ACC oxidase expression and, in turn, preventing ethylene formation. Pelargoniums propagated in culture using the present technique are resistant to wilting and petal shatter, and are morphologically conserved due to the use of petiole explants specifically and the particular culture media disclosed.

DETAILED DESCRIPTION OF THE INVENTION

The present method is a process for propagating plants by tissue culture in such a way as both to conserve desired plant morphology and to transform the plant with respect to one or more desired genes. The method includes the steps of (a) creating an Agrobacterium vector containing the gene sequence desired to be transferred to the propagated plant, preferably together with a marker gene; (b) taking one or more petiole explants from a mother plant and inoculating them with the Agrobacterium vector; (c) conducting callus formation in the petiole sections in culture, in the dark; and (d) culturing the resulting callus in growth medium having a benzylamino growth regulator such as benzylaminopurine or, most preferably, benzylaminopurineriboside. Additional optional growth regulators including auxins and cytokinins (indole butyric acid, benzylamine, benzyladenine, benzylaminopurine, alpha naphthylacetic acid and others known in the art) may also be present. Preferably, the petiole tissue is taken from *Pelargonium x domesticum* and the Agrobacterium vector contains an antisense gene for ACC synthase or ACC oxidase to prevent ACC synthase or ACC oxidase expression and, in turn, preventing ethylene formation. Pelargoniums propagated in culture using the present technique are resistant to wilting and petal shatter, and are morphologically conserved due to the use of petiole explants specifically and the particular culture media disclosed.

Although in theory any anatomic explants can be mixed with Agrobacterium containing the desired gene sequences to be transferred, followed by tissue culture propagation of transgenic transformed plants, in practice we have encountered unexpectedly good results using petioles as the explant tissue. We have found that morphologic conservation is virtually assured with the use of leaf petiole tissue, whereas morphologic variation—even between two generations—can result when explants of other tissue, i.e. leaf tissue, are used. Moreover, the petiole explants should be taken from stock plants (mother plants) of which commercial propagation is desired. Commercial viability is attributable to the large number of transgenically transformed plants which can be produced from a relatively few petioles taken from the mother plant—particularly because leaf petioles can be harvested from a mother plant with impunity, without endangering the mother plant.

The process of the present invention generally proceeds as follows. Leaves are harvested from stock plants for which commercial propagation is desired. The petiole section of each leaf is sterilized with a soap-and-water wash followed by surface sterilization using a solution containing soap and hypochlorite bleach, or a sequence of ethanol and bleach rinses. A good sterilization protocol rinses the petiole tissue in 70% aqueous ethanol for 1 minute, followed by a 15 minute rinse with 10% aqueous bleach, followed by two rinses with sterile water.

After sterilization, the leaf petioles are cut into approximately 1 cm pieces. The cut leaf petioles are inoculated with Agrobacterium cells which contain the gene sequence desired to be transferred to the plant cells, preferably together with a marker gene such as the kanamycin resistance gene known in the art. The inoculation can be as simple as the physical mixing of the cut leaf petioles with the Agrobacterium cells, with an approximate 30 minute incubation at ambient room or greenhouse temperatures.

Those skilled in the art know the significance of the use of a marker gene, but it is instructive to review that technology here. If a genetic sequence to be transplanted includes both the gene (or antisense gene) of interest adjacent a marker gene such as an antibiotic-resistance gene, the successfully genetically transformed cells can easily be separated from any cells in which the desired transformation did not occur. As a practical matter in plant propagation, a number of explants or other regenerative plant cells can be exposed to the gene/marker gene combination and then screened for successful transformants by, for example, inducing and growing the plantlets in culture medium containing the antibiotic for which the marker gene imparts resistance. If any plant grows in the antibiotic-containing medium, it will also have been transformed with respect to the desired gene adjacent the antibiotic-resistance gene. Explants or other cells which may not have underwent genetic transformation merely die in the culture medium—due to antibiotic susceptibility—and disappear.

Those skilled in the art also understand the significance of "antisense" molecular biology, but it should be borne in mind that primarily the present invention is intended to create transformants having antisense genes per se, and preferably not organisms containing vector-borne antisense mRNAs to prevent transcription of intact, or non-antisense, genes. Transformation to create antisense genes is known in the art as exemplified by van der Krol, et al., "Antisense Chalcone Synthase Genes in Petunia Visualization of Variable Transgene Expression," *Mol. Gen. Genet.* (*Molecular & General Genetics*) Vol. 220, No. 2, pp. 204–212 (1990).

The inoculated petiole sections are then transferred to separate test tubes or vials containing culture medium. The culture medium contains vitamins, minerals, a food source and at least one growth regulator. The food source usually includes the Murashige Skoog salt known in the art, and preferably also includes additional food/energy sources, most preferably fresh coconut milk, as well as Agrobacterium virulence enhancers such as acetosyringone. An essential growth regulator is a benzylamino compound chemically equivalent to the most preferred benzylaminopurineriboside or the benzylaminopurines generally. The use of this class of growth regulators gives unexpectedly good results over the use of other growth regulators such as 2,4-dichlorophenoxyacetic acid, kinetin, gibberellic acid, abscisic acid or 6-dimethylallylaminopurine ($N^6$-[2-isopentenyl] adenine). Additional auxin and/or cytokinin growth regulators (indole acetic acid, indole butyric acid, benzylamine, benzyladenine, additional benzylaminopurine, alpha naphthylacetic acid and others) may also be present if they are in addition to, and not in substitution for, the benzyl/amino growth regulator selected.

The test tubes or vials are maintained for five days to two weeks in complete darkness, at a temperature of about 25° C. Over the five day to two week period, the section enlarges slightly and the ends form callus. Miniature shoots start forming intermittently on the callused ends of the petiole section.

After five days to two weeks, the enlarged petiole section bearing the miniature shoots is transferred from the test tube or vial to a Magenta vial or box known in the art. The enlarged petiole sections are housed five-to-a-Magenta vial. The same growing medium as was originally charged to the test tube or vial is likewise charged to the Magenta vial, and in any event coconut milk should be present in the culture medium at this stage of the process. Also added to the medium is kanamycin (assuming the Agrobacterium contained the kanamycin resistance gene) and carbenicillin to kill any excess Agrobacterium. The Magenta vials are then maintained, under the same conditions as were the test tubes or vials, for an additional five to eight weeks in the dark and at about 25° C. The Magenta vials are then exposed to 5–10 weeks of 16 hours of light daily, in which the temperature is maintained at 72° F. with 690 foot candles (6900 lux) of cool fluorescent light. During this time the petiole sections grow into enlarged clumps; the shoots elongate and turn into plantlets and many more shoots form. Once plantlets appear, they are transferred to fresh media containing kanamycin, carbenicillin and no growth hormones.

After the total growth period has elapsed, the clumps are removed and placed in sterile water. The individual plants are dissected out of the clump with a sterile scalpel. Each individual plant essentially has a series of leaves and nodes and is at least ½" high, but usually no roots are present. The individual plants are placed in RUBBER DIRT™ or other soil or soil-like growth media or growth media plugs, where rooting then takes place. Many varieties of *Pelargonium x domesticum* have been successfully tissue cultured through leaf petioles and multiplied, both with and without transgenic transformation via Agrobacterium. Morphologic variation has been minimal and within commercially acceptable limits for finished plant material. Other plants may be propagated by this tissue culture technique/transgenic technique also.

The creation of the Agrobacterium cell containing the desired vector can be accomplished by means known in the art. Structural and regulatory genes to be inserted may be obtained from depositories, such as the American Type Culture Collection, Rockville, Md., 20852, as well as by isolation from other organisms, typically by the screening of genomic or cDNA libraries using conventional hybridization techniques. Typical hybridization techniques are dislosed in Sambrook, et al., *Molecular Cloning—A Laboratory Manual,* Cold Spring Harbor Laboratory, Cold Spring Harbor, N.Y. (1989). Screening may be performed by (1) nucleic acid hybridization using homologous genes or heterologous genes from other organisms, (2) probes synthetically produced to hybridize to particular sequences coding for desired protein sequences, or (3) DNA sequencing and comparison to known sequences. Sequences for specific genes may be found in various computer databases, including GenBank, National Institutes of Health, or the database maintained by the United States Patent and Trademark Office.

The genes of interest may also be identified by antibody screening of expression libraries with antibodies made against homologous proteins to identify genes encoding for homologous functions. Transposon tagging can also be used to aid the isolation of a desired gene. Transposon tagging typically involves mutation of the target gene. A mutant gene is isolated in which a transposon has inserted into the target gene and altered the resulting phenotype. Using a probe for the transposon, the mutated gene can be isolated. Then, using the DNA adjacent to the transposon in the isolated, mutated gene as a probe, the normal wild-type allele of the target gene can be isolated. Such techniques are taught, for example, in McLaughlin and Walbot, *Genetics,* Vol. 117 pp. 771–776 (1987), as well as numerous other references.

In addition to the functional gene and the selectable marker gene, the DNA sequences may also contain a reporter gene which facilitates screening of the transformed shoots and plant material for the presence and expression of endogenous DNA sequences. Exemplary reporter genes include β-glucuronidase and luciferase.

As described above, the exogenous DNA sequences are introduced into the area of the explants by incubation with Agrobacterium cells which carry the sequences to be transferred within a transfer DNA (T-DNA) region found on a suitable plasmid, typically the Ti plasmid. Ti plasmids contain two regions essential for the transformation of plant cells. One of these, the T-DNA region, is transferred to the plant nuclei and induces tumor formation. The other, referred to as the virulence (vir) region, is essential for the transfer of the T-DNA but is not itself transferred. By inserting the DNA sequence to be transferred into the T-DNA region, introduction of the DNA sequences to the plant genome can be effected. Usually, the Ti plasmid will be modified to delete or to inactivate the tumor-causing genes so that they are suitable for use as a vector for the transfer of the gene constructs of the present invention. Other plasmids may be utilized in conjunction with Agrobacterium for transferring the DNA sequences of the present invention to the plant cells.

The construction of recombinant Ti plasmids may be accomplished using conventional recombinant DNA techniques, such as those described by Sambrook et al. (1989). Frequently, the plasmids will include additional selective marker genes which permit manipulation and construction of the plasmids in suitable hosts, typically bacterial hosts other than Agrobacterium, such as *E. coli.* In addition to the above-described kanamycin resistance marker gene, other exemplary genes are the tetracycline resistance gene and the ampicillin resistance gene, among others.

The genes within the DNA sequences will typically be linked to appropriate transcriptional and translational control sequences which are suitable for the Pelargonium plant host. For example, the gene will typically be situated at a distance from a promoter corresponding to the distance at which the promoter is normally effective in order to ensure transcriptional activity. Usually, a polyadenylation site and transcription termination site will be provided at the 3'-end of the gene coding sequence. Frequently, the necessary control functions can be obtained together with the structural gene when it is isolated from a target plant or other host. Such intact genes will usually include coding sequences, intron(s), a promoter, enhancers, and all other regulatory elements either upstream (5') or downstream (3') of the coding sequences.

The binary vector system generally discussed above may be used to introduce the DNA sequence according to the present invention. A first plasmid vector strain would carry the T-DNA sequence while a second plasmid vector carries a virulence (vir) region. By incubating Agrobacterium cells carrying both plasmids with the explant, infection of the plant material is thus achieved.

Any one of a number of T-DNA plasmids can be used with such a binary vector system, the only requirement being that one be able to select independently for the two plasmids. The T-DNA plasmid in a preferred embodiment comprises a heterologous promoter which promotes the transcription of one or more genes within the exogenous DNA fragment(s). An example is the Cauliflower Mosaic Virus 35S promoter (Odell et al., *Nature,* Vol. 313, pp. 810–812 (1985) among others.

Suitable Agrobacterium species include *Agrobacterium tumefaciens* and *Agrobacterium rhizogenes.* While the wild-type *Agrobacterium rhizogenes* may be used, the *Agrobacterium tumefaciens* should be disarmed by deactivating its tumor activating capacity prior to use. Preferred *Agrobacterium tumefaciens* strains include LBA4404, as described by Hoekema et al., Nature, Vol. 303, pp. 179–180 (1983) and EHA101 as described by Hood et al., *J. Bacteriol.,* Vol. 168, pp. 1291–1301 (1986). A preferred *Agrobacterium rhizogenes* strain is 15834, as described by Birot et al., *Plant Physiol. Biochem.,* Vol. 25, pp. 323–325 (1987).

As the Agrobacterium strains carrying the desired exogenous DNA sequences are being prepared, the following antisense sequences are preferred for use in the present process, and are particularly preferred in transforming regal Pelargonium petiole explants according to the present method. These sequences are the known sequences for ACC Synthase (1-aminocyclopropane-1-carboxylate synthase) and ACC Oxidase (1-aminocyclopropane-1-carboxylate oxidase), reversed to create antisense sequences. Tables 1 and 2: show two separate ACC Synthase genes labeled SEQ ID NO:1: and SEQ ID NO:2: respectively. Table 3 shows ACC oxidase gene sequence labeled SEQ ID NO:3:.

After the Agrobacterium strains carrying the desired exogenous DNA sequences have been prepared, they will usually be cultured for a period of time prior to incubation with the explant material. Initially, the Agrobacterium may be cultured on a solid media including nutrients, an energy source and a gelling agent. Suitable nutrients include salts, tryptone and yeast extracts, while most sugars are suitable as the energy source and the gelling agent can be TC agar or bactoagar or other similar products. The Agrobacterium cells are typically cultured for about two to five days, preferably in the dark at about 23–28° C., and are collected by scraping before browning (while still a white color). The cells are scraped from the medium and suspended in a liquid medium such as L-broth, pH 6.9–7.1, preferably 7.0. The bacteria are cultured in liquid medium for 8–36 hours, preferably 12–20, on a shaker (50–220 rpm, preferably 100–120 rpm) at 23–28° C. At the end of this period the bacteria are diluted to an optical density of 0.3 and cultured for 2–6, preferably 4, hours (on a shaker, 23–28° C.). The Agrobacterium cells thus incubated are ready for inoculation onto explant material such as Pelargonium petiole sections.

When Agrobacterium cells are inoculated onto *Pelargonium x domesticum* petiole explants, and after the coincubation discussed above, the tissue culture method will proceed generally in accordance with the disclosure of U.S. application Ser. No. 08/149,702 filed Nov. 9, 1993, which is a Continuation of U.S. application Ser. No. 07/690,073 filed Apr. 23, 1991, by Wendy Oglevee-O'Donovan and Eleanor Stoots, both of which applications are hereby incorporated herein by reference. By means known in the art, carbenicillin can be added to the coincubated petiole/Agrobacterium cells to kill excess Agrobacterium cells, after transfection has taken place. The key is to select an antibiotic which will kill the Agrobacterium without harming the explant material. An additional amount of the same antibiotic may be provided in the ensuing tissue culture method, to assure final removal of any viable Agrobacterium cells.

After green transformed shoots are approximately ½" tall, they can then be transplanted to soil within a greenhouse or elsewhere in a conventional manner for tissue culture plantlets. Transformation of the resulting plantlets can be confirmed by assaying activity for the selection marker, or by assaying the plant material for any of the phenotypes which have been introduced by the exogenous DNA. Suitable assay techniques include polymerase chain reaction (PCR), restriction enzyme digestion, Southern blot hybridization and Northern blot hybridization.

The present invention represents a breakthrough in the commercial production and genetically transformed plants. Because the method uses petiole tissue from a grower's mother plant (a stock plant), the starting petiole explants have a commercially desirable morphology to begin with— by definition. However, if the mother plant could be improved by genetic transformation of some type, for example to deactivate a gene which expresses an enzyme in the ethylene synthesis pathway, the progeny of the mother plant may thus be improved in this one way over their parent stock. The petiole tissue from the stock plant, plus the genetic transformation from the Agrobacterium, yield both an improved genetic makeup of the commercially produced plants—although with preserved desired morphology from the mother plant—and at the same time the high yields possible only with the generation of many plantlets in a single generation's growth in tissue culture. In summary, with the present method a single genetically transformed mother plant can yield literally thousands of offspring plants. No one in the prior art has attempted to combine these two previously disparate technologies to achieve a unique method in which the result is no less than a commercially viable technique for making genetically recombinant plants in commercially feasible numbers (See Example 4).

EXAMPLE 1

*Agrobacterium tumefaciens* strain LBA4404 containing the binary vector pBI 121 which contains the Cauliflower Mosaic Virus 35S promoter with the nptII gene which confers kanamycin resistance and the nos terminator. The Agrobacterium cells were maintained on LB plates containing kanamycin and streptomycin. Overnight suspensions were initiated by the addition of a single colony to 5 ml of LB broth and grown at 28° C. on a shaker in the dark. This example illustrates the preparation of an inoculum from a commercially available binary vector containing *Agrobacterium tumefaciens* strain.

EXAMPLE 2

An aliquot of the inoculum prepared in Example 1 was added to *Pelargonium x domesticum* explants as follows. Petioles were removed from *Pelargonium x domesticum* "Honey" plants and were surface sterilized in a solution containing 70% aqueous ethanol for 1 minute followed by washing in 5% aqueous sodium hypochlorite and 0.1% Tween 20 for 15 minutes. The petiole sections were then rinsed four times using sterile distilled water. Both ends (approximately 3 mm) of the petiole piece were removed and discarded. The remaining petiole was cut into 10 mm segments.

The petiole sections were moved to a flask with enough liquid cocultivation media amply to cover. The cocultivation medium contained vitamins, minerals, a food source, two growth regulators (four parts per million of benzylaminopurineriboside and ten parts per million of indole butyric acid) and sufficient acetosyringone to yield 200 $\mu$M acetosyringone. To this flask was charged the aliquot of Agrobacterium inoculum, and the flask was then swirled for approximately 15 minutes. Additional fresh cocultivation medium plus Agrobacterium inoculum, solidified onto culture plates, was used to receive the explants after pipetting off the liquid cocultivation medium. The plates were incubated in a growth chamber in the dark at 23° C. for three days.

EXAMPLE 3

After conducting Example 2, all explants were washed in liquid media supplemented with 500 $\mu$M cefotaxime for two 1 hour washes. The explants were then transferred to plates containing regeneration media (the cocultivation media minus the acetosyringone and the Agrobacterium), 200 mg/l kanamycin, and 500 mg/l carbenicillin solidified with 0.26 Gelrite. The petri dishes were wrapped in parafilm and grown in a growth chamber in the dark at 23° C. After 3–5 weeks, untransformed tissue became dark brown and died. Small "buds" appeared on transformed tissue after 4–6 weeks. After approximately 6–7 weeks tissue containing shoots was transferred to magenta vessels containing regeneration medium, 200 mg/l kanamycin, and 500 mg/l carbenicillin solidified with 0.2% Gelrite. The Magenta vessels were then transferred to a growth room and grown under periods of light and dark wherein 16 hours of dark was followed by 8 hours of light, then 16 hours of dark and so on. When the shoots were 2–3 cm tall, they were transferred to magenta vessels containing rooting media. Rooted shoots were then acclimated to a greenhouse environment. Six transformed plants were produced on selection medium. NPT assays, GUS assays, and Southern blot analysis were used for confirmation of transformed Pelargoniums.

EXAMPLE 4

Using Agrobacterium containing the appropriate vectors, petiole explants from *Pelargonium x domesticum* are transformed for insertion of one of the following antisense genes: antisense ACC Synthase or antisense ACC Oxidase. Except for this alternate genetic transformation, the remaining steps proceed according to Examples 1–3.

EXAMPLE 5

Forty petioles are taken from a transformed *Pelargonium x domesticum* stock plant according to Example 4. Each petiole is divided into 4 segments to make 160 explants. The explants are grown in culture according to Examples 1–3. With an average of 30 plantlets per cultured petiole segment, the total production from the transformed stock plant is thus 4800 offspring plants (160×30) without even beginning to exhaust the available petiole tissue from the stock plant.

TABLE 1

SEQ ID NO:1: GAC-1

```
tatcactactctcgcttctgagtgcctaattatttttgtccaagctctcagtacgtacgtgttgtacgtgtttacata
gATGGAGAACAAGAGCAAACAGCTTCTGTCAAAGATTGCAACCAACGACGGACACGGCGAGAACTCCCCATATTTCGA
  M   E   N   K   S   K   Q   L   L   S   K   I   A   T   N   D   G   H   G   E   N   S   P   Y   F   D TGGTTGGAAGGCTTATGACCGTGATCCGTTCCATCCGTCTCAGAATCCTAACGGTGTTATCCAGATGGGTTTAGCTGA
  G   W   K   A   Y   D   R   D   P   F   H   P   S   Q   N   P   N   G   V   I   Q   M   G   L   A   E OLE-2                                                                OLE-5
AAATCAGCTTTCATCTGACTTGATTGAAGATTGGGTGAGGTCCAACCCAGAAGCCTCAATCTGCACTCTTGAGGGAGT    312
  N   Q   L   S   S   D   L   I   E   D   W   V   R   S   N   P   E   A   S   I   C   T   L   E   G   V TGGTAAGTTCAAGGACGTAGCTAACTTTCAGGACTACCATGGCCTGCTGGAGTTCAGGCACGCCGTGGCTAAATTTAT
  G   K   F   K   D   V   A   N   F   Q   D   Y   H   G   L   L   E   F   R   H   A   V   A   K   F   M OLE-3
GAGCAGAGGAAGGGCGGGAAGGTCACATTTGATCCCGACCGTGTCGTCATGAGCGGCGGAGCCACCGGAGCCAACGA     468
  S   R   G   R   G   G   K   V   T   F   D   P   D   R   V   V   M   S   G   G   A   T   G   A   N   E GCTCATCGTCTTCTGTTTGGCCAATCCCGGCGACGCTTTCCTTCTCCCATCTCCTTATTATCCAGCAAACGACCGTGA
  L   I   V   F   C   L   A   N   P   G   D   A   F   L   I   P   S   P   Y   Y   P   A   N   D   R   D CTTGCAGTGGCGAACCGGAGCTCAGATCATTCCGGTGCACTGCAACAGCTCCAACGGTTTCAAGATAACCAGAGAGGC    624
  L   Q   W   R   T   G   A   Q   I   I   P   V   H   C   N   S   S   N   G   F   K   I   T   R   E   A ACTAGAAAGATCATACGCACAAGCACAAGAAAGCAACATAAACGTAAAAGGCGTGCTCTTAACCAACCCATCGAACCC
  L   E   R   S   Y   A   Q   A   Q   E   S   N   I   N   V   K   G   V   L   L   T   N   P   S   N   P TCTAGACACAATTCTGGACCGCGACACTCTCAAGAGCATCGTCAGCTTCGTCACCGACAACAACATCCACCTAGTCAT    780
  L   G   T   I   L   D   R   D   T   L   K   S   I   V   S   F   V   T   D   N   N   I   H   L   V   I CGACGAAATCTACGCCGCCACCGTTTTCGTTGCCCCGGAGTTCGTAAGCGTCTCCGAAATCCTCCAAGAAATGGACGA
  D   E   I   Y   A   A   T   V   F   V   A   P   E   P   V   S   V   S   E   I   L   Q   E   M   D   D CACCACGTGCAACCCCGACCTCATCCACATCGTGTACAGCCTGTCCAAGGACTTGGGCATGCCCGGGTTCCGCGTCGG    936
  T   T   C   N   P   D   L   I   H   I   V   Y   S   L   S   K   D   L   G   M   P   G   F   R   V   G GATCGTGTACTCATTCAACGACGACGTCGTATCCTGCGCACGGAAGATGTCGAGCTTCGGGTTGGTGTCGACCCAGAC
  I   V   Y   S   F   N   D   D   V   V   S   C   A   R   K   M   S   S   F   G   L   V   S   T   Q   T GCAGCACCTTCTCGCAGCGATGCTATCCGACGACGTTTTCGTGGAGCGGTTCCTCGCGGAGCGGAGGCGGTTGGGGAG   1092
  Q   H   L   L   A   A   M   L   S   D   D   V   F   V   E   R   F   L   A   E   R   R   R   L   G   R GAGGCACGGCGTGTTCACGAAAGGCTCGAGGAGTTGGGGATTGGGTGTTTAAAGAGCAACGCGGGGCTCTACTTCTG
  R   H   G   V   F   T   K   G   L   E   E   L   G   I   G   C   L   K   S   N   A   G   L   Y   F   W GATGGATTTGCGGAAGCTTCTAGAAGAAGAGACGTTTGAGGCGGAGATGGTGCTGTGGAAGGTGATTATTAATGAGGT   1248
  M   D   L   R   K   L   L   E   E   E   T   F   E   A   E   M   V   L   W   K   V   I   I   N   E   V GAAGCTAAACGTGTCTCCGGGGTCGTCGTTTCATTGCGTGGAGCCGGGTTGGTTTAGGGTTTGCTTTGCCAACATGGA
  K   L   N   V   S   P   G   S   S   F   H   C   V   E   P   G   W   F   R   V   C   F   A   N   M   D
                                                                                            OLE-4

OLE-6
CGACGAGACGGTCCACGTGGCGCTGAAGAGGATCAGGGCGTTTGTGAGGAAGAAGGAGGTGGGTCCGGTGAAGAGGAA   1404
  D   E   T   V   H   V   A   L   K   R   I   R   A   F   V   R   K   K   E   V   G   P   V   K   R   K

GAGGTTCATGGACAACCTTAACCTCAGGCTGAGCTTCTCGTCGCTAAGGTACGATGAGAGTGTGATGTTGTCGCCGCA
```

TABLE 1-continued

SEQ ID NO:1: GAC-1

```
   R  F  M  D  N  L  N  L  R  L  S  F  S  S  L  R  Y  D  E  S  V  M  L  S  P  H

CATAATGGTGTCCACGCACTCGCCGCTTGTTCGTGCGAGAACAtaatgagcatgcacgttttttatttgctactgttag      1560
   I  M  V  S  T  H  S  P  L  V  R  A  R  T taattaactaattaattgttatttgattgtgtgctgaatgttggattctttctttgtagaagagaagctataggagat gtttttaaccaattaccgtagatatatatgcagtggaattaagaaaaatagaggttaaatattaattccatgcatata      1716 tatgtaggaaggaattggtacatattttagggtttgctgatgttttctttcatcatgaattggtacatatttatgatg ttcaaggctccaagtgatggatacatggaggattcatttggatgcatgccttgcaagagtcagcaatgtttgttaatt      1872 agtgtatggtttgtgataataaagatgcaaaattctgtgttgttttaaaaaaaaaaaaaaa                        1934
```

TABLE 2

SEQ ID NO:2: GAC-2

```
TATTTTGATGGGTGGAAGGCTTACGACAACAATCCTTTCCATCTCACCCAAAACCCTCAAGGTGTCATCCAGATGGGC
 Y  F  D  G  W  K  A  Y  D  N  N  P  F  H  L  T  Q  N  P  Q  G  V  I  Q  M  G
    OLE-2
CTCGCAGAAAATCAGCTTTCTTTCGAGTTGATTGAGCAATGGGTCCTTAACAACCCACAAGCCTCCATTTGCACAGCA     156
 L  A  E  N  Q  L  S  F  E  L  I  E  Q  W  V  L  N  N  P  Q  A  S  I  C  T  A
OLE-5
CAAGGTCTGCAAGAATTCAAGGACACTGCAATCTTTCAAGATTACCATGGCTTGCCAGAGTTCAGATATGCTGTTGCA
 Q  G  L  Q  E  F  K  D  T  A  I  F  Q  D  Y  H  G  L  P  E  F  R  Y  A  V  A

AATTTCATGGGAAAGGTGAGAGGAAACAGAGTAACATTTAACCCAGATCGCATAGTTATGAGTGGAGGAGCAACTGGA     312
 N  F  M  G  K  V  R  G  N  R  V  T  F  N  P  D  R  I  V  M  S  G  G  A  T  G

GCTCATGAAATGATTGCCTTCTGTTTGGCTGATCCTGGCGATGCTTTTCTTGTCCCAACTGGTTATTATCCTGGATTT
 A  H  E  M  I  A  F  C  L  A  D  P  G  D  A  F  L  V  P  T  P  Y  Y  P  G  F

GATAGAGACCTGAGGTGGAGAACTGGTGTGCAGCTAATTCCTGTAGTCTGTGAAAGTGAAAACAATTTCAGGATCACC     468
 D  R  D  L  R  W  R  T  G  V  Q  L  I  P  V  V  C  E  S  E  N  N  F  R  I  T

CGAAGTGCCTTAGAAGAAGCCTATGAGAGAGCTCAAGAGGACAACATTAGAGTCAAGGGATTGCTCATAACAAACCCA
 R  S  A  L  E  E  A  Y  E  R  A  Q  E  D  N  I  R  V  K  G  L  L  I  T  N  P

TCAAACCCACTAGGAACTATCCTGGACAGAGAGACACTGGTCAGTCTAGTGAGCTTCATCAATGAAAAGAACATTCAC     624
 S  N  P  L  G  T  I  L  D  R  E  T  L  V  S  L  V  S  F  I  N  E  K  N  I  H

TTGGTCTGTGATGAAATCTACGCCGCCACAGTGTTGTCTCAGCCCGCTTTCGTTAGCATTGCTGAGGTTATCGAGCAA
 L  V  C  D  E  I  Y  A  A  T  V  F  S  Q  P  A  F  V  S  I  A  E  V  I  E  Q

GAGAACGTTTCGTGCAACCGCGACCTCATCCACATTGTCTACAGCCTGTCCAAGGACATGGGCTTCCCTGGCTTCAGG     780
 E  N  V  S  C  N  R  D  L  I  H  I  V  Y  S  L  S  K  D  M  G  F  P  G  F  R

GTGGGGATTGTCTACTCCTACAATGACGCAGTTGTGAATTGTGCGCGAAAGATGTCAAGTTTCGGCCTTGTATCCACA
 V  G  I  V  Y  S  Y  N  D  A  V  V  N  C  A  R  K  M  S  S  F  G  L  V  S  T

CAAACTCAGCACCTAATCGCATCAATGCTCTCGGACGATGAATTCGTGGACACATTCATCGTGGAGAGCGCGAAGAGG     936
 Q  T  Q  H  L  I  A  S  M  L  S  D  D  E  F  V  D  T  F  I  V  E  S  A  K  R

CTAGCGAGAAGGTACGCAACCTTCACAAGAGGGCTTGCACAAGTCCACATTGGGAGCCTAAAGAGCAATGGGGGGTTA
 L  A  R  R  Y  A  T  F  T  R  G  L  A  Q  V  H  I  G  S  L  K  S  N  G  G  L

TTCATATGGATGGACTTGAGGAGGCTTCTCAAGGAGAAGACTTTCGAGGCGGAGATGGCTCTGTGGAGAGTGATAATC     1092
 F  I  W  M  D  L  R  R  L  L  K  E  K  T  F  E  A  E  M  A  L  W  R  V  I  I

AATGAGGTGAACGTAAATGTGTCGCCAGGGGCGTCGTTCCATTGCTCGGAGCCAGGGTGGTTCAGAGTCTGTTTCGCT     1170
 N  E  V  K  L  N  V  S  P  G  A  S  F  H  C  S  E  P  G  W  F  R  V  C  F  A
                                                                       OLE-6
```

TABLE 3

SEQ ID NO:3: GEFE-1

```
cttgagtcttgagtgtgtgttagcaagaaacaaacattagtgtgaaaacacaagagaaggagaaaaaaataccttgct tttattggagATGGAGAGCTTTCCAGTGATCAACATGGAGAAGTTGAATGGTGAGGAGAGAGCAGCAACCATGGAGAA      156
            M  E  S  F  P  V  I  N  M  E  K  L  N  G  E  E  R  A  A  T  M  E  K
GATCAAGGATGCTTGTGAAAACTGGGGTTTTTTTGAGCTGTTGAACCATGGGATACCCTATGAGCTGCTTGACACAGT
 I  K  D  A  C  E  N  W  G  F  F  E  L  L  N  H  G  I  P  Y  E  L  L  D  T  V      49
P0
GGAGAAGATGACAAAGGAGCATTACAGGAAGTGTATGGAGCAGAGGTTTAAGGAAATGGTGGCAAGCAAGGGACTTGA      312
 E  K  M  T  K  E  H  Y  R  K  C  M  E  Q  R  F  K  E  M  V  A  S  K  G  L  E
AGGAGTGGAGGTAGAGGTTGAGGACTTGGATTGGGAGAGCACTTTTTTCTTGAAGCATCTCCCAGAATCAAACATCTC
    G  V  E  V  E  D  L  D  W  E  S  T  F  F  L  K  H  L  P  E  S  N  I  S       101
TCAAGTCCCTGATCTTCAAGACGAGTACAGGAAGGTGATGAAGGAATTTGCAGCAAAACTAGAGAAACTAGCCGAGGA      468
 Q  V  P  D  L  Q  D  E  Y  R  K  V  M  K  E  F  A  A  K  L  E  K  L  A  E  E
GCTACTAGACCTGTTGAGCGAGAATCTTGGGdTAGAGAAAGGTTACCTGAAAAAAGCTTTCTATGGCTCAAAGGGTCC
 L  L  D  L  L  S  E  N  L  G  L  E  K  G  Y  L  K  K  A  F  Y  G  S  K  G  P    153
AACCTTTGGCACCAAGGTCAGCAACTACCCTCCCTGCCCCAAGCCAGACTTAATCAAGGGACTCAGGGCACATACAGA      624
 T  F  G  T  K  V  S  N  Y  P  P  C  P  K  P  D  L  I  K  G  L  R  A  H  T  D
TGCCGGAGGCCTCATATTGCTCTTCCAAGACGACAAGGTCAGTGGTCTCCAGCTCCTGAAAGACGGGAAGTGGGTCGA
 A  G  G  L  I  L  L  F  Q  D  D  K  V  S  G  L  Q  L  L  K  D  G  K  W  V  D    205
TGTTCCTCCTATGCACCACTCCATCGTCATCAACCTCGGTGACCAACTTGAGGTGATTACCAATGGGAAATACAAGAG      780
 V  P  P  M  H  H  S  I  V  I  N  L  G  D  Q  L  E  V  I  T  N  G  K  Y  K  S
CATAGAGCACCGTGTGATAGCCCAATCAGACGGTACTAGAATGTCCATTGCTTCCTTCTACAACCCGGGAAGTGATGC
 I  E  H  R  V  I  A  Q  S  D  G  T  R  M  S  I  A  S  F  Y  N  P  G  S  D  A    257
GGTCATCTATCCAGCACCAGCTCTGTTGGAGAAAGAAACAGAAGAGAAGCAAGTGTACCCGAAATTCGTGTTCGAAGA      936
 V  I  Y  P  A  P  A  L  L  E  K  E  T  E  E  K  Q  V  Y  P  K  F  V  F  E  D
CTACATGAAGCTCTACTCTGGCCTCAAGTTCCAAGCCAAAGAGCCCAGATTTGAAGCCATGAAAGCTGTGGAGGCTAA
 Y  M  K  L  Y  S  G  L  K  F  Q  A  K  E  P  R  F  E  A  M  K  A  V  E  A  N    309
TGTTACTTTGGATCCAATTCGAACTGCCtagaaagatattatacaacaaccttagcagatcagaaagaagaagaacaa    1092
 V  T  L  D  P  I  R  T  A                                                         318
agggtagactgtgttgtctgttcttaaggtggttgtgttgtgtccaggctgctaaaagctttgtgatttgttttttaaa
ttttatgacgcacggcttactataatgggttctttatcagtttgtttatagtcatgggtgctaattatttggtattat    1248
aatatataagagtattagtcaaaaaaaaaaaaaaaaaaaaaaa                                        1291
```

Although the invention has been described with particularity above, especially in the Examples, this disclosure is illustrative only and the invention is thus to be limited only insofar as is set forth in the accompanying claims.

---

What is claimed is:

1. A method for commercially producing transgenic Pelargonium plants, comprising:
   harvesting at least one petiole from a mother plant;
   inoculating said petiole with a vector within an Agrobacterium bacteria and genetically transforming at least one cell in said petiole;
   culturing the transformed petiole tissue thus produced in a culture medium comprising at least one benzylaminoglycoside growth regulator and with exposure to periods of light and dark; and
   removing small plants generated by the transformed petiole tissue to conditions which permit its further rooting and growth.

2. The method according to claim 1 wherein said culture medium comprises benzylaminopurineriboside.

3. The method according to claim 1 wherein the Agrobacterium vector comprises an antisense ACC Synthase gene.

4. The method according to claim 1 wherein the Agrobacterium vector comprises an antisense ACC Oxidase gene.

5. The method according to claim 3 or 4 wherein said Agrobacterium vector further comprises a marker gene.

6. A method for commercially producing transgenic *Pelargonium x domesticum* plants, comprising:
   harvesting at least one petiole from a *Pelargonium x domesticum* mother plant;
   inoculating said petiole with a vector within an Agrobacterium bacteria and genetically transforming at least one cell in said petiole;
   culturing the transformed petiole tissue thus produced in a culture medium comprising at least one benzylaminoglycoside growth regulator and with exposure to periods of light and dark; and
   removing small plants generated by the transformed petiole tissue to conditions which permit its further rooting and growth.

7. The method according to claim 6 wherein said culture medium comprises a growth regulator selected from the group consisting of benzylaminopurineriboside and benzylaminopurine.

8. The method according to claim 6 wherein the Agrobacterium vector comprises an antisense ACC Synthase gene.

9. The method according to claim 6 wherein the Agrobacterium vector comprises an antisense ACC Oxidase gene.

10. The method according to claim 8 or 9 wherein said Agrobacterium vector further comprises a marker gene.

11. The method according to claim 10 wherein the inoculating step is conducted by cocultivating said petiole and said Agrobacterium in a medium comprises benzylaminopurineriboside growth regulator.

12. The method according to claim 10 wherein said marker gene is the kanamycin resistance gene.

13. The method according to claim 12 wherein said Agrobacterium vector further comprises a nucleic acid sequence which is antisense to the sense sequence of SEQ ID NO:1.

14. The method according to claim 12 wherein said Agrobacterium vector further comprises a nucleic acid sequence which is antisense to the sense sequence of SEQ ID NO:2.

15. The method according to claim 12 wherein said Agrobacterium vector further comprises a nucleic acid sequence which is antisense to the sense sequence of SEQ ID NO:3.

16. The product prepared in accordance with the method of claim 1.

17. The product prepared in accordance with the method of claim 6.

* * * * *

UNITED STATES PATENT AND TRADEMARK OFFICE
CERTIFICATE OF CORRECTION

PATENT NO. : 6,610,909 B1
DATED : August 26, 2003
INVENTOR(S) : Wendy Oglevee-O'Donovan et al.

It is certified that error appears in the above-identified patent and that said Letters Patent is hereby corrected as shown below:

<u>Title page,</u>
Item [75], Inventors, "Scottsdale" should read -- Scottdale --.

<u>Column 9,</u>
Line 7, "2:" should read -- 2 --.

<u>Column 10,</u>
Line 61, "0.26" should read -- 0.2% --.

Signed and Sealed this

Seventeenth Day of February, 2004

JON W. DUDAS
*Acting Director of the United States Patent and Trademark Office*

SEQUENCE LISTING

```
<160> NUMBER OF SEQ ID NOS: 6

<210> SEQ ID NO 1
<211> LENGTH: 1934
<212> TYPE: DNA
<213> ORGANISM: Pelargonium x hortorum
<220> FEATURE:
<221> NAME/KEY: CDS
<222> LOCATION: (80)..(1525)

<400> SEQUENCE: 1
tatcactact ctcgcttctg agtgcctaat tatttttgtc caagctctca gtacgtacgt      60
gttgtacgtg tttacatag atg gag aac aag agc aaa cag ctt ctg tca aag    112
                        Met Glu Asn Lys Ser Lys Gln Leu Leu Ser Lys
                          1               5                  10
```

-continued

| | |
|---|---|
| att gca acc aac gac gga cac ggc gag aac tcc cca tat ttc gat ggt<br>Ile Ala Thr Asn Asp Gly His Gly Glu Asn Ser Pro Tyr Phe Asp Gly<br>15                    20                    25 | 160 |
| tgg aag gct tat gac cgt gat ccg ttc cat ccg tct cag aat cct aac<br>Trp Lys Ala Tyr Asp Arg Asp Pro Phe His Pro Ser Gln Asn Pro Asn<br>30                    35                    40 | 208 |
| ggt gtt atc cag atg ggt tta gct gaa aat cag ctt tca tct gac ttg<br>Gly Val Ile Gln Met Gly Leu Ala Glu Asn Gln Leu Ser Ser Asp Leu<br>45                    50                    55 | 256 |
| att gaa gat tgg gtg agg tcc aac cca gaa gcc tca atc tgc act ctt<br>Ile Glu Asp Trp Val Arg Ser Asn Pro Glu Ala Ser Ile Cys Thr Leu<br>60                    65                    70                    75 | 304 |
| gag gga gtt ggt aag ttc aag gac gta gct aac ttt cag gac tac cat<br>Glu Gly Val Gly Lys Phe Lys Asp Val Ala Asn Phe Gln Asp Tyr His<br>80                    85                    90 | 352 |
| ggc ctg ctg gag ttc agg cac gcc gtg gct aaa ttt atg agc aga gga<br>Gly Leu Leu Glu Phe Arg His Ala Val Ala Lys Phe Met Ser Arg Gly<br>95                    100                  105 | 400 |
| agg ggc ggg aag gtc aca ttt gat ccc gac cgt gtc gtc atg agc ggc<br>Arg Gly Gly Lys Val Thr Phe Asp Pro Asp Arg Val Val Met Ser Gly<br>110                    115                  120 | 448 |
| gga gcc acc gga gcc aac gag ctc atc gtc ttc tgt ttg gcc aat ccc<br>Gly Ala Thr Gly Ala Asn Glu Leu Ile Val Phe Cys Leu Ala Asn Pro<br>125                    130                  135 | 496 |
| ggc gac gct ttc ctt ctc cca tct cct tat tat cca gca aac gac cgt<br>Gly Asp Ala Phe Leu Leu Pro Ser Pro Tyr Tyr Pro Ala Asn Asp Arg<br>140                    145                  150                  155 | 544 |
| gac ttg cag tgg cga acc gga gct cag atc att ccg gtg cac tgc aac<br>Asp Leu Gln Trp Arg Thr Gly Ala Gln Ile Ile Pro Val His Cys Asn<br>160                    165                  170 | 592 |
| agc tcc acc ggt ttc aag ata acc aga gag gca cta gaa aga tca tac<br>Ser Ser Thr Gly Phe Lys Ile Thr Arg Glu Ala Leu Glu Arg Ser Tyr<br>175                    180                  185 | 640 |
| gca caa gca caa gaa agc aac ata aac gta aaa ggc gtg ctc tta acc<br>Ala Gln Ala Gln Glu Ser Asn Ile Asn Val Lys Gly Val Leu Leu Thr<br>190                    195                  200 | 688 |
| aac cca tcg aac cct cta gac aca att ctg gac cgc gac act ctc aag<br>Asn Pro Ser Asn Pro Leu Asp Thr Ile Leu Asp Arg Asp Thr Leu Lys<br>205                    210                  215 | 736 |
| agc atc gtc agc ttc gtc acc gac aac aac atc cac cta gtc atc gac<br>Ser Ile Val Ser Phe Val Thr Asp Asn Asn Ile His Leu Val Ile Asp<br>220                    225                  230                  235 | 784 |
| gaa atc tac gcc gcc acc gtt ttc gtt gcc ccg gag ttc gta agc gtc<br>Glu Ile Tyr Ala Ala Thr Val Phe Val Ala Pro Glu Phe Val Ser Val<br>240                    245                  250 | 832 |
| tcc gaa atc ctc caa gaa atg gac gac acc acg tgc aac ccc gac ctc<br>Ser Glu Ile Leu Gln Glu Met Asp Asp Thr Thr Cys Asn Pro Asp Leu<br>255                    260                  265 | 880 |
| atc cac atc gtg tac agc ctg tcc aag gac ttg ggc atg ccc ggg ttc<br>Ile His Ile Val Tyr Ser Leu Ser Lys Asp Leu Gly Met Pro Gly Phe<br>270                    275                  280 | 928 |
| cgc gtc ggg atc gtg tac tca ttc aac gac gac gtc gta tcc tgc gca<br>Arg Val Gly Ile Val Tyr Ser Phe Asn Asp Asp Val Val Ser Cys Ala<br>285                    290                  295 | 976 |
| cgg aag atg tcg agc ttc ggg ttg gtg tcg acc cag acg cag cac ctt<br>Arg Lys Met Ser Ser Phe Gly Leu Val Ser Thr Gln Thr Gln His Leu<br>300                    305                  310                  315 | 1024 |
| ctc gca gcg atg cta tcc gac gac gtt ttc gtg gag cgg ttc ctc gcg<br>Leu Ala Ala Met Leu Ser Asp Asp Val Phe Val Glu Arg Phe Leu Ala<br>320                    325                  330 | 1072 |

```
gag cgg agg cgg ttg ggg agg agg cac ggc gtg ttc acg aaa ggg ctc      1120
Glu Arg Arg Arg Leu Gly Arg Arg His Gly Val Phe Thr Lys Gly Leu
            335                 340                 345
gag gag ttg ggg att ggg tgt tta aag agc aac gcg ggg ctc tac ttc      1168
Glu Glu Leu Gly Ile Gly Cys Leu Lys Ser Asn Ala Gly Leu Tyr Phe
        350                 355                 360
tgg atg gat ttg cgg aag ctt cta gaa gaa gag acg ttt gag gcg gag      1216
Trp Met Asp Leu Arg Lys Leu Leu Glu Glu Glu Thr Phe Glu Ala Glu
    365                 370                 375
atg gtg ctg tgg aag gtg att att aat gag gtg aag cta aac gtg tct      1264
Met Val Leu Trp Lys Val Ile Ile Asn Glu Val Lys Leu Asn Val Ser
380                 385                 390                 395
ccg ggg tcg tcg ttt cat tgc gtg gag ccg ggt tgg ttt agg gtt tgc      1312
Pro Gly Ser Ser Phe His Cys Val Glu Pro Gly Trp Phe Arg Val Cys
                400                 405                 410
ttt gcc aac atg gac gac gag acg gtc cac gtg gcg ctg aag agg atc      1360
Phe Ala Asn Met Asp Asp Glu Thr Val His Val Ala Leu Lys Arg Ile
            415                 420                 425
agg gcg ttt gtg agg aag aag gag gtg ggt ccg gtg aag agg aag agg      1408
Arg Ala Phe Val Arg Lys Lys Glu Val Gly Pro Val Lys Arg Lys Arg
        430                 435                 440
ttc atg gac aac ctt aac ctc agg ctg agc ttc tcg tcg cta agg tac      1456
Phe Met Asp Asn Leu Asn Leu Arg Leu Ser Phe Ser Ser Leu Arg Tyr
    445                 450                 455
gat gag agt gtg atg ttg tcg ccg cac ata atg gtg tcc acg cac tcg      1504
Asp Glu Ser Val Met Leu Ser Pro His Ile Met Val Ser Thr His Ser
460                 465                 470                 475
ccg ctt gtt cgt gcg aga aca taatgagcat gcacgttttt atttgctact         1555
Pro Leu Val Arg Ala Arg Thr
                480 gttagtaatt aactaattaa ttgttatttg attgtgtgct gaatgttgga ttctttcttt    1615 gtagaagaga agctatagga gatgttttta accaattacc gtagatatat atgcagtgga    1675 attaagaaaa atagaggtta aatattaatt ccatgcatat atatgtagga aggaattggt    1735 acatatttta gggtttgctg atgttttctt tcatcatgaa ttggtacata tttatgatgt    1795 tcaaggctcc aagtgatgga tacatggagg attcatttgg atgcatgcct tgcaagagtc    1855 agcaatcttt gttaattagt gtatggtttg tgataataaa gatgcaaaat tctgtgttgt    1915 tttaaaaaaa aaaaaaaaa                                                 1934

<210> SEQ ID NO 2
<211> LENGTH: 482
<212> TYPE: PRT
<213> ORGANISM: Pelargonium x hortorum

<400> SEQUENCE: 2

Met Glu Asn Lys Ser Lys Gln Leu Leu Ser Lys Ile Ala Thr Asn Asp
 1               5                  10                  15

Gly His Gly Glu Asn Ser Pro Tyr Phe Asp Gly Trp Lys Ala Tyr Asp
            20                  25                  30

Arg Asp Pro Phe His Pro Ser Gln Asn Pro Asn Gly Val Ile Gln Met
        35                  40                  45

Gly Leu Ala Glu Asn Gln Leu Ser Ser Asp Leu Ile Glu Asp Trp Val
    50                  55                  60

Arg Ser Asn Pro Glu Ala Ser Ile Cys Thr Leu Glu Gly Val Gly Lys
65                  70                  75                  80

Phe Lys Asp Val Ala Asn Phe Gln Asp Tyr His Gly Leu Leu Glu Phe
```

-continued

```
                85                  90                  95
Arg His Ala Val Ala Lys Phe Met Ser Arg Gly Arg Gly Gly Lys Val
                    100                 105                 110

Thr Phe Asp Pro Asp Arg Val Val Met Ser Gly Gly Ala Thr Gly Ala
                115                 120                 125

Asn Glu Leu Ile Val Phe Cys Leu Ala Asn Pro Gly Asp Ala Phe Leu
            130                 135                 140

Leu Pro Ser Pro Tyr Tyr Pro Ala Asn Asp Arg Asp Leu Gln Trp Arg
145                 150                 155                 160

Thr Gly Ala Gln Ile Ile Pro Val His Cys Asn Ser Ser Thr Gly Phe
                    165                 170                 175

Lys Ile Thr Arg Glu Ala Leu Glu Arg Ser Tyr Ala Gln Ala Gln Glu
                180                 185                 190

Ser Asn Ile Asn Val Lys Gly Val Leu Leu Thr Asn Pro Ser Asn Pro
            195                 200                 205

Leu Asp Thr Ile Leu Asp Arg Asp Thr Leu Lys Ser Ile Val Ser Phe
210                 215                 220

Val Thr Asp Asn Asn Ile His Leu Val Ile Asp Glu Ile Tyr Ala Ala
225                 230                 235                 240

Thr Val Phe Val Ala Pro Glu Phe Val Ser Val Ser Glu Ile Leu Gln
                    245                 250                 255

Glu Met Asp Asp Thr Thr Cys Asn Pro Asp Leu Ile His Ile Val Tyr
                260                 265                 270

Ser Leu Ser Lys Asp Leu Gly Met Pro Gly Phe Arg Val Gly Ile Val
            275                 280                 285

Tyr Ser Phe Asn Asp Asp Val Val Ser Cys Ala Arg Lys Met Ser Ser
290                 295                 300

Phe Gly Leu Val Ser Thr Gln Thr Gln His Leu Leu Ala Ala Met Leu
305                 310                 315                 320

Ser Asp Asp Val Phe Val Glu Arg Phe Leu Ala Glu Arg Arg Arg Leu
                    325                 330                 335

Gly Arg Arg His Gly Val Phe Thr Lys Gly Leu Glu Glu Leu Gly Ile
                340                 345                 350

Gly Cys Leu Lys Ser Asn Ala Gly Leu Tyr Phe Trp Met Asp Leu Arg
            355                 360                 365

Lys Leu Leu Glu Glu Glu Thr Phe Glu Ala Glu Met Val Leu Trp Lys
370                 375                 380

Val Ile Ile Asn Glu Val Lys Leu Asn Val Ser Pro Gly Ser Ser Phe
385                 390                 395                 400

His Cys Val Glu Pro Gly Trp Phe Arg Val Cys Phe Ala Asn Met Asp
                    405                 410                 415

Asp Glu Thr Val His Val Ala Leu Lys Arg Ile Arg Ala Phe Val Arg
                420                 425                 430

Lys Lys Glu Val Gly Pro Val Lys Arg Lys Phe Met Asp Asn Leu
            435                 440                 445

Asn Leu Arg Leu Ser Phe Ser Ser Leu Arg Tyr Asp Glu Ser Val Met
        450                 455                 460

Leu Ser Pro His Ile Met Val Ser Thr His Ser Pro Leu Val Arg Ala
465                 470                 475                 480

Arg Thr

<210> SEQ ID NO 3
<211> LENGTH: 1170
```

```
<212> TYPE: DNA
<213> ORGANISM: Pelargonium x hortorum
<220> FEATURE:
<221> NAME/KEY: CDS
<222> LOCATION: (1)..(1170)

<400> SEQUENCE: 3 tat ttt gat ggg tgg aag gct tac gac aac aat cct ttc cat ctc acc      48
Tyr Phe Asp Gly Trp Lys Ala Tyr Asp Asn Asn Pro Phe His Leu Thr
 1               5                  10                  15 caa aac cct caa ggt gtc atc cag atg ggc ctc gca gaa aat cag ctt      96
Gln Asn Pro Gln Gly Val Ile Gln Met Gly Leu Ala Glu Asn Gln Leu
             20                  25                  30 tct ttc gag ttg att gag caa tgg gtc ctt aac aac cca caa gcc tcc     144
Ser Phe Glu Leu Ile Glu Gln Trp Val Leu Asn Asn Pro Gln Ala Ser
         35                  40                  45 att tgc aca gca caa ggt ctg caa gaa ttc aag gac act gca atc ttt     192
Ile Cys Thr Ala Gln Gly Leu Gln Glu Phe Lys Asp Thr Ala Ile Phe
     50                  55                  60 caa gat tac cat ggc ttg cca gag ttc aga tat gct gtt gca aat ttc     240
Gln Asp Tyr His Gly Leu Pro Glu Phe Arg Tyr Ala Val Ala Asn Phe
 65                  70                  75                  80 atg gga aag gtg aga gga aac aga gta aca ttt aac cca gat cgc ata     288
Met Gly Lys Val Arg Gly Asn Arg Val Thr Phe Asn Pro Asp Arg Ile
                 85                  90                  95 gtt atg agt gga gga gca act gga gct cat gaa atg att gcc ttc tgt     336
Val Met Ser Gly Gly Ala Thr Gly Ala His Glu Met Ile Ala Phe Cys
            100                 105                 110 ttg gct gat cct ggc gat gct ttt ctt gtc cca act cct tat tat cct     384
Leu Ala Asp Pro Gly Asp Ala Phe Leu Val Pro Thr Pro Tyr Tyr Pro
        115                 120                 125 gga ttt gat aga gac ctg agg tgg aga act ggt gtg cag cta att cct     432
Gly Phe Asp Arg Asp Leu Arg Trp Arg Thr Gly Val Gln Leu Ile Pro
    130                 135                 140 gta gtc tgt gaa agt gaa aac aat ttc agg atc acc cga agt gcc tta     480
Val Val Cys Glu Ser Glu Asn Asn Phe Arg Ile Thr Arg Ser Ala Leu
145                 150                 155                 160 gaa gaa gcc tat gag aga gct caa gag gac aac att aga gtc aag gga     528
Glu Glu Ala Tyr Glu Arg Ala Gln Glu Asp Asn Ile Arg Val Lys Gly
                165                 170                 175 ttg ctc ata aca aac cca tca aac cca cta gga act atc ctg gac aga     576
Leu Leu Ile Thr Asn Pro Ser Asn Pro Leu Gly Thr Ile Leu Asp Arg
            180                 185                 190 gag aca ctg gtc agt cta gtg agc ttc atc aat gaa aag aac att cac     624
Glu Thr Leu Val Ser Leu Val Ser Phe Ile Asn Glu Lys Asn Ile His
        195                 200                 205 ttg gtc tgt gat gaa atc tac gcc gcc aca gtc ttc tct cag ccc gct     672
Leu Val Cys Asp Glu Ile Tyr Ala Ala Thr Val Phe Ser Gln Pro Ala
    210                 215                 220 ttc gtt agc att gct gag gtt atc gag caa gag aac gtt tcg tgc aac     720
Phe Val Ser Ile Ala Glu Val Ile Glu Gln Glu Asn Val Ser Cys Asn
225                 230                 235                 240 cgc gac ctc atc cac att gtc tac agc ctg tcc aag gac atg ggc ttc     768
Arg Asp Leu Ile His Ile Val Tyr Ser Leu Ser Lys Asp Met Gly Phe
                245                 250                 255 cct ggc ttc agg gtg ggg att gtc tac tcc tac aat gac gca gtt gtg     816
Pro Gly Phe Arg Val Gly Ile Val Tyr Ser Tyr Asn Asp Ala Val Val
            260                 265                 270 att tgt gcg cga aag atg tca agt ttc ggc ctt gta tcc aca caa act     864
Ile Cys Ala Arg Lys Met Ser Ser Phe Gly Leu Val Ser Thr Gln Thr
        275                 280                 285
```

```
cag cac cta atc gca tca atg ctc tcg gac gat gaa ttc gtg gac aca    912
Gln His Leu Ile Ala Ser Met Leu Ser Asp Asp Glu Phe Val Asp Thr
    290                 295                 300 ttc atc gtg gag agc gcg aag agg cta gcg aga agg tac gca acc ttc    960
Phe Ile Val Glu Ser Ala Lys Arg Leu Ala Arg Arg Tyr Ala Thr Phe
305                 310                 315                 320 aca aga ggg ctt gca caa gtc cac att ggg agc cta aag agc aat ggg   1008
Thr Arg Gly Leu Ala Gln Val His Ile Gly Ser Leu Lys Ser Asn Gly
                325                 330                 335 ggg tta ttc ata tgg atg gac ttg agg agg ctt ctc aag gag aag act   1056
Gly Leu Phe Ile Trp Met Asp Leu Arg Arg Leu Leu Lys Glu Lys Thr
            340                 345                 350 ttc gag gcg gag atg gct ctg tgg aga gtg ata atc aat gag gtg aag   1104
Phe Glu Ala Glu Met Ala Leu Trp Arg Val Ile Ile Asn Glu Val Lys
        355                 360                 365 cta aat gtg tcg cca ggg gcg tcg ttc cat tgc tcg gag cca ggg tgg   1152
Leu Asn Val Ser Pro Gly Ala Ser Phe His Cys Ser Glu Pro Gly Trp
    370                 375                 380 ttc aga gtc tgt ttc gct                                            1170
Phe Arg Val Cys Phe Ala
385                 390

<210> SEQ ID NO 4
<211> LENGTH: 390
<212> TYPE: PRT
<213> ORGANISM: Pelargonium x hortorum

<400> SEQUENCE: 4

Tyr Phe Asp Gly Trp Lys Ala Tyr Asp Asn Asn Pro Phe His Leu Thr
 1               5                  10                  15

Gln Asn Pro Gln Gly Val Ile Gln Met Gly Leu Ala Glu Asn Gln Leu
            20                  25                  30

Ser Phe Glu Leu Ile Glu Gln Trp Val Leu Asn Asn Pro Gln Ala Ser
        35                  40                  45

Ile Cys Thr Ala Gln Gly Leu Gln Glu Phe Lys Asp Thr Ala Ile Phe
    50                  55                  60

Gln Asp Tyr His Gly Leu Pro Glu Phe Arg Tyr Ala Val Ala Asn Phe
65                  70                  75                  80

Met Gly Lys Val Arg Gly Asn Arg Val Thr Phe Asn Pro Asp Arg Ile
                85                  90                  95

Val Met Ser Gly Gly Ala Thr Gly Ala His Glu Met Ile Ala Phe Cys
            100                 105                 110

Leu Ala Asp Pro Gly Asp Ala Phe Leu Val Pro Thr Pro Tyr Tyr Pro
        115                 120                 125

Gly Phe Asp Arg Asp Leu Arg Trp Arg Thr Gly Val Gln Leu Ile Pro
    130                 135                 140

Val Val Cys Glu Ser Glu Asn Asn Phe Arg Ile Thr Arg Ser Ala Leu
145                 150                 155                 160

Glu Glu Ala Tyr Glu Arg Ala Gln Glu Asp Asn Ile Arg Val Lys Gly
                165                 170                 175

Leu Leu Ile Thr Asn Pro Ser Asn Pro Leu Gly Thr Ile Leu Asp Arg
            180                 185                 190

Glu Thr Leu Val Ser Leu Val Ser Phe Ile Asn Glu Lys Asn Ile His
        195                 200                 205

Leu Val Cys Asp Glu Ile Tyr Ala Ala Thr Val Phe Ser Gln Pro Ala
    210                 215                 220
```

-continued

```
Phe Val Ser Ile Ala Glu Val Ile Glu Gln Glu Asn Val Ser Cys Asn
225                 230                 235                 240

Arg Asp Leu Ile His Ile Val Tyr Ser Leu Ser Lys Asp Met Gly Phe
                245                 250                 255

Pro Gly Phe Arg Val Gly Ile Val Tyr Ser Tyr Asn Asp Ala Val Val
            260                 265                 270

Ile Cys Ala Arg Lys Met Ser Ser Phe Gly Leu Val Ser Thr Gln Thr
        275                 280                 285

Gln His Leu Ile Ala Ser Met Leu Ser Asp Asp Glu Phe Val Asp Thr
    290                 295                 300

Phe Ile Val Glu Ser Ala Lys Arg Leu Ala Arg Arg Tyr Ala Thr Phe
305                 310                 315                 320

Thr Arg Gly Leu Ala Gln Val His Ile Gly Ser Leu Lys Ser Asn Gly
                325                 330                 335

Gly Leu Phe Ile Trp Met Asp Leu Arg Arg Leu Leu Lys Glu Lys Thr
            340                 345                 350

Phe Glu Ala Glu Met Ala Leu Trp Arg Val Ile Ile Asn Glu Val Lys
        355                 360                 365

Leu Asn Val Ser Pro Gly Ala Ser Phe His Cys Ser Glu Pro Gly Trp
    370                 375                 380

Phe Arg Val Cys Phe Ala
385                 390
```

```
<210> SEQ ID NO 5
<211> LENGTH: 1291
<212> TYPE: DNA
<213> ORGANISM: Pelargonium x hortorum
<220> FEATURE:
<221> NAME/KEY: CDS
<222> LOCATION: (89)..(1042)

<400> SEQUENCE: 5
cttgagtctt gagtgtgtgt tagcaagaaa caaacattag tgtgaaaaca caagagaagg    60
agaaaaaaat accttgcttt tattggag atg gag agc ttt cca gtg atc aac     112
                              Met Glu Ser Phe Pro Val Ile Asn
                                1               5 atg gag aag ttg aat ggt gag gag aga gca gca acc atg gag aag atc    160
Met Glu Lys Leu Asn Gly Glu Glu Arg Ala Ala Thr Met Glu Lys Ile
 10                  15                  20 aag gat gct tgt gaa aac tgg ggt ttt ttt gag ctg ttg aac cat ggg    208
Lys Asp Ala Cys Glu Asn Trp Gly Phe Phe Glu Leu Leu Asn His Gly
 25                  30                  35                  40 ata ccc tat gag ctg ctt gac aca gtg gag aag atg aca aag gag cat    256
Ile Pro Tyr Glu Leu Leu Asp Thr Val Glu Lys Met Thr Lys Glu His
                 45                  50                  55 tac agg aag tgt atg gag cag agg ttt aag gaa atg gtg gca agc aag    304
Tyr Arg Lys Cys Met Glu Gln Arg Phe Lys Glu Met Val Ala Ser Lys
             60                  65                  70 gga ctt gaa gga gtg gag gta gag gtt gag gac ttg gat tgg gag agc    352
Gly Leu Glu Gly Val Glu Val Glu Val Glu Asp Leu Asp Trp Glu Ser
         75                  80                  85 act ttt ttc ttg aag cat ctc cca gaa tca aac atc tct caa gtc cct    400
Thr Phe Phe Leu Lys His Leu Pro Glu Ser Asn Ile Ser Gln Val Pro
     90                  95                 100 gat ctt caa gac gag tac agg aag gtg atg aag gaa ttt gca gca aaa    448
Asp Leu Gln Asp Glu Tyr Arg Lys Val Met Lys Glu Phe Ala Ala Lys
105                 110                 115                 120 cta gag aaa cta gcc gag gag cta cta gac ctg ttg agc gag aat ctt    496
```

```
                                                                                  Leu Glu Lys Leu Ala Glu Glu Leu Leu Asp Leu Leu Ser Glu Asn Leu
                                                    125                 130                 135 ggg cta gag aaa ggt tac ctg aaa aaa gct ttc tat ggc tca aag ggt              544
Gly Leu Glu Lys Gly Tyr Leu Lys Lys Ala Phe Tyr Gly Ser Lys Gly
        140                 145                 150 cca acc ttt ggc acc aag gtc agc aac tac cct ccc tgc ccc aag cca              592
Pro Thr Phe Gly Thr Lys Val Ser Asn Tyr Pro Pro Cys Pro Lys Pro
            155                 160                 165 gac tta atc aag gga ctc agg gca cat aca gat gcc gga ggc ctc ata              640
Asp Leu Ile Lys Gly Leu Arg Ala His Thr Asp Ala Gly Gly Leu Ile
        170                 175                 180 ttg ctc ttc caa gac gac aag gtc agt ggt ctc cag ctc ctg aaa gac              688
Leu Leu Phe Gln Asp Asp Lys Val Ser Gly Leu Gln Leu Leu Lys Asp
185                 190                 195                 200 ggg aag tgg gtc gat gtt cct cct atg cac cac tcc atc gtc atc aac              736
Gly Lys Trp Val Asp Val Pro Pro Met His His Ser Ile Val Ile Asn
                    205                 210                 215 ctc ggt gac caa ctt gag gtg att acc aat ggg aaa tac aag agc ata              784
Leu Gly Asp Gln Leu Glu Val Ile Thr Asn Gly Lys Tyr Lys Ser Ile
                220                 225                 230 gag cac cgt gtg ata gcc caa tca gac ggt act aga atg tcc att gct              832
Glu His Arg Val Ile Ala Gln Ser Asp Gly Thr Arg Met Ser Ile Ala
        235                 240                 245 tcc ttc tac aac ccg gga agt gat gcg gtc atc tat cca gca cca gct              880
Ser Phe Tyr Asn Pro Gly Ser Asp Ala Val Ile Tyr Pro Ala Pro Ala
    250                 255                 260 ctg ttg gag aaa gaa aca gaa gag aag caa gtg tac ccg aaa ttc gtg              928
Leu Leu Glu Lys Glu Thr Glu Glu Lys Gln Val Tyr Pro Lys Phe Val
265                 270                 275                 280 ttc gaa gac tac atg aag ctc tac tct ggc ctc aag ttc caa gcc aaa              976
Phe Glu Asp Tyr Met Lys Leu Tyr Ser Gly Leu Lys Phe Gln Ala Lys
                    285                 290                 295 gag ccc aga ttt gaa gcc atg aaa gct gtg gag gct aat gtt act ttg             1024
Glu Pro Arg Phe Glu Ala Met Lys Ala Val Glu Ala Asn Val Thr Leu
                300                 305                 310 gat cca att cga act gcc tagaaagata ttatacaaca accttagcag                    1072
Asp Pro Ile Arg Thr Ala
            315 atcagaaaga agaagaacaa agggtagact gtgttgtctg ttcttaaggt ggttgtgttg           1132 tgtccaggct gctaaaagct ttgtgatttg tttttaaatt ttatgacgca cggcttacta           1192 taatgggttc tttatcagtt tgtttatagt catgggtgct aattatttgg tattataata           1252 tataagagta ttagtcaaaa aaaaaaaaaa aaaaaaaaa                                  1291

<210> SEQ ID NO 6
<211> LENGTH: 318
<212> TYPE: PRT
<213> ORGANISM: Pelargonium x hortorum

<400> SEQUENCE: 6

Met Glu Ser Phe Pro Val Ile Asn Met Glu Lys Leu Asn Gly Glu Glu
  1               5                  10                  15

Arg Ala Ala Thr Met Glu Lys Ile Lys Asp Ala Cys Glu Asn Trp Gly
             20                  25                  30

Phe Phe Glu Leu Leu Asn His Gly Ile Pro Tyr Glu Leu Leu Asp Thr
         35                  40                  45

Val Glu Lys Met Thr Lys Glu His Tyr Arg Lys Cys Met Glu Gln Arg
     50                  55                  60
```

-continued

```
Phe Lys Glu Met Val Ala Ser Lys Gly Leu Glu Gly Val Glu Val Glu
 65                  70                  75                  80

Val Glu Asp Leu Asp Trp Glu Ser Thr Phe Phe Leu Lys His Leu Pro
                 85                  90                  95

Glu Ser Asn Ile Ser Gln Val Pro Asp Leu Gln Asp Glu Tyr Arg Lys
                100                 105                 110

Val Met Lys Glu Phe Ala Ala Lys Leu Glu Lys Leu Ala Glu Glu Leu
            115                 120                 125

Leu Asp Leu Leu Ser Glu Asn Leu Gly Leu Glu Lys Gly Tyr Leu Lys
            130                 135                 140

Lys Ala Phe Tyr Gly Ser Lys Gly Pro Thr Phe Gly Thr Lys Val Ser
145                 150                 155                 160

Asn Tyr Pro Pro Cys Pro Lys Pro Asp Leu Ile Lys Gly Leu Arg Ala
                165                 170                 175

His Thr Asp Ala Gly Gly Leu Ile Leu Leu Phe Gln Asp Asp Lys Val
                180                 185                 190

Ser Gly Leu Gln Leu Leu Lys Asp Gly Lys Trp Val Asp Val Pro Pro
            195                 200                 205

Met His His Ser Ile Val Ile Asn Leu Gly Asp Gln Leu Glu Val Ile
    210                 215                 220

Thr Asn Gly Lys Tyr Lys Ser Ile Glu His Arg Val Ile Ala Gln Ser
225                 230                 235                 240

Asp Gly Thr Arg Met Ser Ile Ala Ser Phe Tyr Asn Pro Gly Ser Asp
                245                 250                 255

Ala Val Ile Tyr Pro Ala Pro Ala Leu Leu Glu Lys Glu Thr Glu Glu
            260                 265                 270

Lys Gln Val Tyr Pro Lys Phe Val Phe Glu Asp Tyr Met Lys Leu Tyr
            275                 280                 285

Ser Gly Leu Lys Phe Gln Ala Lys Glu Pro Arg Phe Glu Ala Met Lys
            290                 295                 300

Ala Val Glu Ala Asn Val Thr Leu Asp Pro Ile Arg Thr Ala
305                 310                 315
```